(12) United States Patent
Tatarkiewicz

(10) Patent No.: US 9,857,283 B1
(45) Date of Patent: Jan. 2, 2018

(54) METHOD FOR CALIBRATING INVESTIGATED VOLUME FOR LIGHT SHEET BASED NANOPARTICLE TRACKING AND COUNTING APPARATUS

(71) Applicant: MANTA Instruments, Inc., San Diego, CA (US)

(72) Inventor: Jan J. Tatarkiewicz, San Diego, CA (US)

(73) Assignee: Manta Instruments, Inc., San Diego, CA (US)

( * ) Notice: Subject to any disclaimer, the term of this patent is extended or adjusted under 35 U.S.C. 154(b) by 0 days.

(21) Appl. No.: 15/634,858

(22) Filed: Jun. 27, 2017

Related U.S. Application Data

(60) Provisional application No. 62/372,025, filed on Aug. 8, 2016, provisional application No. 62/357,777, filed
(Continued)

(51) Int. Cl.
| | | |
|---|---|---|
| *G01N 15/02* | (2006.01) | |
| *G01N 15/10* | (2006.01) | |
| *G01N 15/14* | (2006.01) | |
| *G01N 21/51* | (2006.01) | |
| *G02B 21/06* | (2006.01) | |

(Continued)

(52) U.S. Cl.
CPC ..... *G01N 15/1012* (2013.01); *G01N 15/0227* (2013.01); *G01N 15/1463* (2013.01); *G01N 21/51* (2013.01); *G02B 21/06* (2013.01); *G02B 21/365* (2013.01); *G01N 2015/0038* (2013.01); *G01N 2015/1486* (2013.01);
(Continued)

(58) Field of Classification Search
CPC . G01J 3/10; G01N 15/1012; G01N 2015/003; G01N 15/0227; G01N 15/1463; G01N 21/51; G01N 2015/0038; G01N 2015/1486; G01N 2021/513; G01N 2021/127; G01N 15/0211; G02B 21/06; G02B 21/365; H04N 7/181

USPC .................................................. 356/335–343
See application file for complete search history.

(56) References Cited

U.S. PATENT DOCUMENTS

| | | | |
|---|---|---|---|
| 4,274,740 A | 6/1981 | Eidenschink et al. | |
| 5,650,847 A * | 7/1997 | Maltsev ................. | G01N 15/14 356/336 |

(Continued)

FOREIGN PATENT DOCUMENTS

WO 2010055280 5/2010

OTHER PUBLICATIONS

Internatioanl Search Report dated Sep. 13, 2017 for PCT/US2017/039819.

*Primary Examiner* — Tri T Ton
(74) *Attorney, Agent, or Firm* — Manuel de la Cerra

(57) ABSTRACT

A method for calibrating a dark field microcopy setup is disclosed. The method includes preparing a plurality of particle samples, each with a known concentration and particle size, the plurality having more than one particle size and, optionally, more than one refractive index and more than one diluent. For each sample in the plurality, the sample is measured in the setup and the scattered light intensity and number of particles is measured. From this data, a relationship between the scattered light intensity, particle size and calibrated investigated volume can be determined. The calibrated investigated volume is used to obtain the proper particle size distribution in a given diluent.

12 Claims, 19 Drawing Sheets

Related U.S. Application Data on Jul. 1, 2016, provisional application No. 62/421,585, filed on Nov. 14, 2016.

(51) Int. Cl.
*G02B 21/36* (2006.01)
*G01N 15/00* (2006.01)
*H04N 7/18* (2006.01)

(52) U.S. Cl.
CPC . *G01N 2021/513* (2013.01); *G01N 2201/127* (2013.01); *H04N 7/181* (2013.01)

(56) References Cited

U.S. PATENT DOCUMENTS

| | | | |
|---|---|---|---|
| 6,970,243 B2 | 11/2005 | Togawa | |
| 7,009,169 B2 | 3/2006 | Wong et al. | |
| 2009/0222218 A1 | 9/2009 | Chamberlin et al. | |
| 2009/0244536 A1* | 10/2009 | Mitchell | G01N 15/1459 356/343 |
| 2011/0214489 A1* | 9/2011 | Grant | G01N 1/4077 73/61.72 |
| 2012/0293799 A1* | 11/2012 | Lerche | G01N 15/042 356/337 |

* cited by examiner

| Mean diameter [nm] | Average volume [1/m³] | Gravimetric concentration [1/mL] | Beads in mix [µL] | Mili-Q in mix [mL] | Master via gravi [1/mL] | Master dilution [x] | Estimated concentration [1/mL] | Full dilution [x] |
|---|---|---|---|---|---|---|---|---|
| 30 | 1.41E-23 | 6.74E+14 | 20 | 20 | 6.73E+11 | 34,000 | 1.98E+07 | 34,034,000 |
| 40 | 3.35E-23 | 2.84E+14 | 20 | 20 | 2.84E+11 | 14,000 | 2.03E+07 | 14,014,000 |
| 46 | 5.10E-23 | 1.87E+14 | 20 | 20 | 1.87E+11 | 9,000 | 2.07E+07 | 9,009,000 |
| 70 | 1.80E-22 | 5.30E+13 | 20 | 20 | 5.30E+10 | 2,600 | 2.04E+07 | 2,602,600 |
| 81 | 2.78E-22 | 3.42E+13 | 20 | 20 | 3.42E+10 | 1,700 | 2.01E+07 | 1,701,700 |
| 100 | 5.24E-22 | 1.82E+13 | 20 | 20 | 1.82E+10 | 900 | 2.02E+07 | 900,900 |
| 152 | 1.84E-21 | 5.18E+12 | 20 | 20 | 5.17E+09 | 250 | 2.07E+07 | 250,250 |
| 203 | 4.38E-21 | 2.17E+12 | 20 | 20 | 2.17E+09 | 100 | 2.17E+07 | 100,100 |
| 303 | 1.46E-20 | 6.54E+11 | 20 | 20 | 6.53E+08 | 33 | 1.98E+07 | 33,033 |
| 400 | 3.35E-20 | 2.84E+11 | 20 | 20 | 2.84E+08 | 14 | 2.03E+07 | 14,014 |
| 496 | 6.39E-20 | 1.49E+11 | 20 | 20 | 1.49E+08 | 7 | 2.13E+07 | 7,007 |
| 600 | 1.13E-19 | 8.42E+10 | 20 | 20 | 8.41E+07 | 4 | 2.10E+07 | 4,004 |
| 702 | 1.81E-19 | 5.26E+10 | 20 | 20 | 5.25E+07 | 3 | 1.75E+07 | 3,003 |
| 799 | 2.67E-19 | 3.57E+10 | 20 | 20 | 3.56E+07 | 2 | 1.78E+07 | 2,002 |
| 903 | 3.86E-19 | 2.47E+10 | 20 | 20 | 2.47E+07 | 1 | 2.47E+07 | 1,001 |

FIG. 5

METHOD FOR CALIBRATING INVESTIGATED VOLUME FOR LIGHT SHEET BASED NANOPARTICLE TRACKING AND COUNTING APPARATUS

1.0 RELATED APPLICATIONS

This application claims priority to U.S. Provisional Patent Application No. 62/357,777 filed on Jul. 1, 2016, titled "METHOD FOR CALIBRATING INVESTIGATED VOLUME FOR LIGHT SHEET BASED NANOPARTICLE TRACKING AND COUNTING APPARATUS"; priority to U.S. Provisional Patent Application No. 62/372,025 filed on Aug. 8, 2016, titled "METHOD FOR CALIBRATING INVESTIGATED VOLUME FOR LIGHT SHEET BASED NANOPARTICLE TRACKING AND COUNTING APPARATUS"; and priority to U.S. Provisional Patent Application No. 62/421,585 filed on Nov. 14, 2016, titled "METHOD FOR CALIBRATING INVESTIGATED VOLUME FOR LIGHT SHEET BASED NANOPARTICLE TRACKING AND COUNTING APPARATUS", the disclosures of all of which are herein incorporated by reference in their entirety.

This application is also related to U.S. Provisional Patent Application No. 62/241,354 filed on Oct. 14, 2015, titled "APPARATUS FOR MEASUREMENTS OF GROWTH OR DISSOLUTION KINETICS OF COLLOIDAL NANOPARTICLE"; U.S. patent application Ser. No. 15/293,180, filed on Oct. 16, 2016, titled "APPARATUS AND METHOD FOR MEASUREMENT OF GROWTH OR DISSOLUTION KINETICS OF COLLOIDAL PARTICLES"; U.S. patent application Ser. No. 15/018,532 filed on Feb. 8, 2016, titled "MULTI-CAMERA APPARATUS FOR OBSERVATION OF MICROSCOPIC MOVEMENTS AND COUNTING OF PARTICLES IN COLLOIDS AND ITS CALIBRATION"; U.S. patent application Ser. No. 15/194,823, filed on Jun. 28, 2016, titled "SPECIAL PURPOSE CUVETTE ASSEMBLY AND METHOD FOR OPTICAL MICROSCOPY OF NANOPARTICLES IN LIQUIDS" issued on Jan. 10, 2017 as U.S. Pat. No. 9,541,490; U.S. patent application Ser. No. 14/730,138, filed on Jun. 3, 2015, titled "NANOPARTICLE ANALYZER", issued on May 9, 2017 as U.S. Pat. No. 9,645,070; U.S. patent application Ser. No. 15/399,679, filed on Jan. 5, 2017, titled "SPECIAL PURPOSE CUVETTE ASSEMBLY AND METHOD FOR OPTICAL MICROSCOPY OF NANOPARTICLES IN LIQUIDS"; U.S. patent application Ser. No. 15/594,967, filed on May 15, 2017, titled "SPECIAL PURPOSE CUVETTE ASSEMBLY AND METHOD FOR OPTICAL MICROSCOPY OF NANOPARTICLES IN LIQUIDS"; and U.S. Patent Application No. 62/187,391 filed on Jul. 1, 2015, titled "SPECIAL PURPOSE CUVETTE ASSEMBLY AND METHOD FOR OPTICAL MICROSCOPY OF NANOPARTICLES IN LIQUIDS"; the disclosures of all of which are herein incorporated by reference in their entirety.

2.0 TECHNICAL FIELD

The present invention relates to measurement and observations of nanoparticles in liquid samples using a microscope equipped with digital video camera.

3.0 BACKGROUND

Nanoparticles are ubiquitous and by far the most abundant particle-like entities in natural environments on Earth and are widespread across many applications associated with human activities. There are many types of naturally occurring nanoparticles and man-made (engineered) nanoparticles. Nanoparticles occur in air, aquatic environments, rain water, drinking water, bio-fluids, pharmaceuticals, drug delivery and therapeutic products, and a broad range of many industrial products. Nanoparticles usually occur within poly-disperse assemblages, which are characterized by co-occurrence of differently-sized particles.

Given the widespread usage of nanoparticles, the ability to control and accurately characterize their properties may be useful to many applications. Conventional methods for measuring nanoparticle properties may be inaccurate for poly-disperse samples of mixed nanoparticle sizes, which are common in many applications. Some of these conventional approaches make measurements on an ensemble of a large number of nanoparticles within a sample. Because the light scattered from all nanoparticles is measured simultaneously, it may be difficult to resolve the nanoparticles into their constituent sizes when there is a range of particle sizes. Other approaches fail to account for the large differences in the intensity of scattered light produced by differently-sized nanoparticles across the range of nanoparticle sizes. In these approaches, the low scattering signals from small nanoparticles may be undetected, or the high scattering signals from larger nanoparticles can obscure the signals from smaller nanoparticles. And in yet other approaches, the measurements fail to account for the growth rate or dissolution rate of the particles, such that a snap-shot of a size distribution could be inaccurate a few moments later. As a result of these deficiencies, the concentration of nanoparticles of any given size, and hence the entire size distribution, can be subject to unknown error.

These methods of detecting nanoparticles are commonly referred as dark field microscopy. An instrument setup 10 is shown in FIGS. 1A and 1B to perform such an analysis. The setup typically comprises: a light source 15 that produces light beam 20 that passes through cylindrical lens and an optical objective 25 that form a light sheet 30, which is directed at a small cell (cuvette) 35. The cuvette 35 contains the nanoparticles in a colloid made out of a diluent, some of them being observed within the investigated volume 38. The nanoparticles in the investigative volume 38 scatter light 40 that is directed through a focusing optical objective 45 (which may also include magnifying optical objectives—i.e., a microscope), producing a focused light beam 50 onto a sensor (e.g., camera) 55. A processor 60 may be connected to the sensor 55 and the light source 15 to control them. The setup 10 enables illumination of any liquid with a precisely-formed, narrow light sheet and observation of scattered light from the nanoparticles, usually at a 90-degree angle relative to the light sheet plane. In other words, the direction of observation is perpendicular to the direction of the plane of illumination.

Different sized particles can be visualized owing to the camera capturing reflected light images from the particles, with such images having different intensities (various brightness of pixels comprising an image) based on the size of particles and their composition (refractive index different than refractive index of a diluent). By tracking images of scattered light on subsequent frames of recorded videos and using theory of Brownian motion (Einstein's equation), one can determine size of each observed particle individually (this is usually called Nanoparticle Tracking Analysis or NTA). Since one can count and size all observed particles, in principle particle size distribution (PSD) can be also calculated accurately. Typically, to obtain such distribution one bins sizes of particles, i.e. adds number of all particles that have sizes within a certain range of diameters and places them in separate bins corresponding to this range of diameters. To obtain PSD, the number of particles in each bin is divided by the corresponding bin width and by the investigated volume.

The problem with this method is the non-uniformity of light intensity of the light sheet that is being used to visualize particles for tracking and counting. The area observed by the camera is easily calibrated by using microscales to find exact calibration constant, i.e. number of length units per camera pixel, as shown in FIG. 2. An ideal light sheet would have a "top hat" light intensity characteristic 65—i.e., there will be a sharp border between illuminated and dark regions (volumes) of a sample as shown in FIG. 3. However, optical devices used to produce light sheets like lasers, lens and objectives, typically generate Gaussian-like profiles 70 of light intensity—see FIG. 3 showing "top hat" distribution 65 as compared to a Gaussian distribution (same intensity or area under both curves). Depending on light scattering cross section for a given particle material in a given diluent and the camera sensitivity (quantum efficiency), the effective light sheet thickness, and thus investigated volume, can vary considerably (particles being closer to the edge of light sheet receive less light for scattering and thus possibly are not being detected by the apparatus). This variable investigative volume will highly influence the determination of PSD or concentration of particles in a colloid unless it is properly accounted for.

Therefore, a need exists for properly calibrating the investigated volume for different types and different sizes of particles. This size/type dependent investigated volume can then be used to arrive at a more precise determination of PSD or particle concentration for any colloid.

4.0 SUMMARY

The following presents a simplified summary in order to provide a basic understanding of some aspects of the claimed subject matter. This summary is not an extensive overview, and is not intended to identify key/critical elements or to delineate the scope of the claimed subject matter. Its purpose is to present some concepts in a simplified form as a prelude to the more detailed description that is presented later.

The apparatus, systems, and methods described herein elegantly solve the problems presented above. A method for calibrating the investigated volume in a dark field microcopy setup is disclosed. The setup comprises a light source constructed to emit a beam of electromagnetic radiation at a specimen chamber, the chamber is constructed to hold the colloidal particles and to allow a portion of the beam to scatter perpendicularly to the beam entering the chamber, the scattered portion of the beam is directed into a sensor, wherein the sensor is adapted to detect the electromagnetic radiation. This includes preparing a plurality of particle samples with known concentrations and particle sizes, the plurality having more than one particle size and, optionally, more than one refractive index and more than one diluent. For each sample in the plurality, the sample is introduced into the specimen chamber, the light source is activated and the scattered light intensity and number of particles detected by the sensor are recorded. A relationship between the scattered light intensity and, optionally, the sample's refractive index relative to refractive index of diluent for each particle size in the plurality is determined. Also, a relationship between a calibrated investigated volume and, optionally, the sample's refractive index in various diluents for each particle size in the plurality, based on the number of particles measured for the sample, is determined.

The relationship for scattered light intensity vs. relative refractive index of particles and diluent, and investigated volume vs. relative refractive index (RI), can be extrapolated for particle sizes that possess unknown relative RI in the same diluent. The method may be used to create a three-dimensional relationship between the scattered light intensity, particle size and investigated volume for a given diluent.

The method can be performed at a variety of light source wavelengths, and a four-dimensional relationship between the light source wavelength, the scattered light intensity, particle size and investigated volume may be determined for various diluents.

Based on the determined relationships (i.e., scattered light intensity vs. relative refractive index of particles in a diluent, and investigated volume vs. relative refractive index), the particle size distribution of an unknown sample can be calculated more accurately. The unknown sample in a known diluent is introduced into the specimen chamber and the light source is activated. For each of the plurality of particle sizes in the unknown sample, the scattered light intensity and a number of particles are measured on the images recorded by the sensor. And for each particle size a calibrated investigated volume is determined based on the predetermined relationships for the setup. Then an accurate particle size distribution based on the calibrated investigated volumes can be determined.

These methods can be automated and run on a processor connected to the sensor.

Additional aspects, alternatives and variations as would be apparent to persons of skill in the art are also disclosed herein and are specifically contemplated as included as part of the invention. The invention is set forth only in the claims as allowed by the patent office in this or related applications, and the following summary descriptions of certain examples are not in any way to limit, define or otherwise establish the scope of legal protection.

5.0 BRIEF DESCRIPTION OF THE DRAWINGS

The invention can be better understood with reference to the following figures. The components within the figures are not necessarily to scale, emphasis instead being placed on clearly illustrating example aspects of the invention. In the figures reference numerals designate corresponding parts throughout the different views and/or embodiments. It will be understood that certain components and details may not appear in the figures to assist in more clearly describing the invention.

Figure 3:
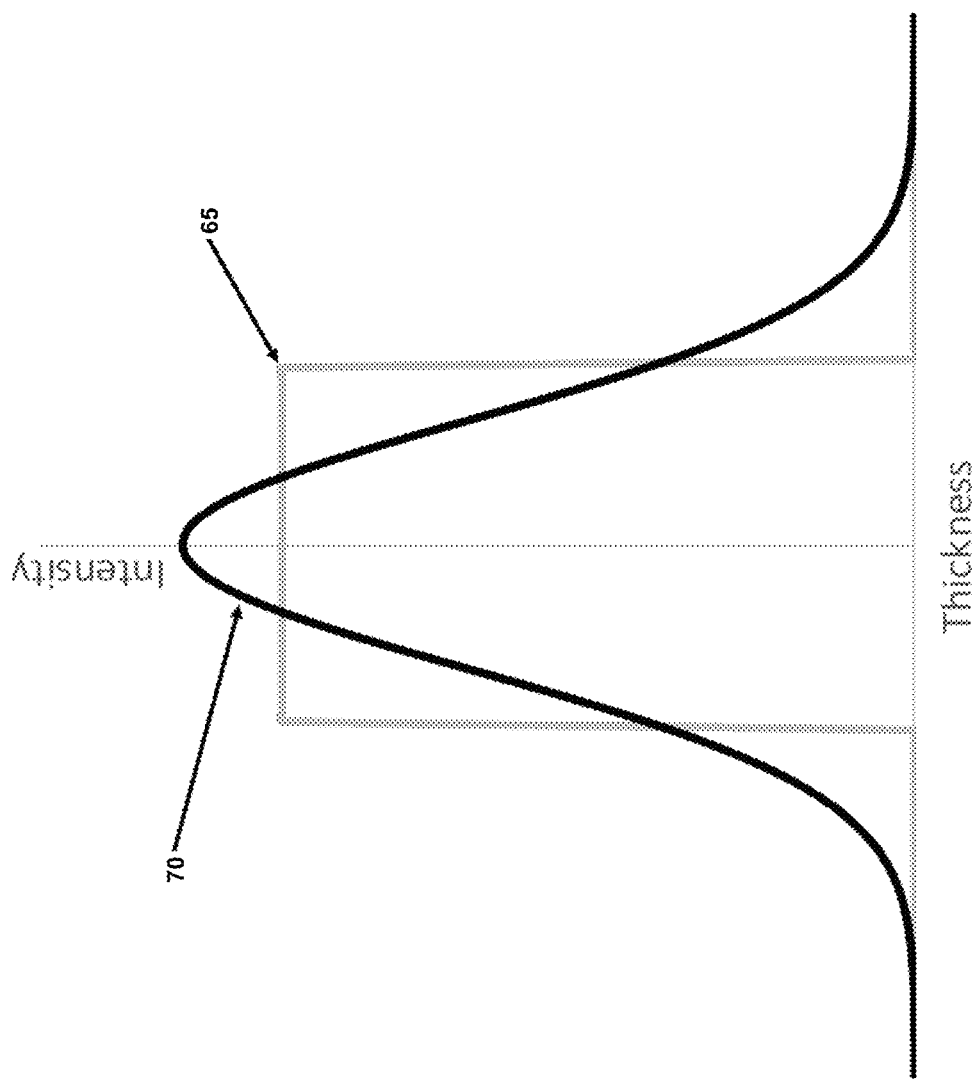

FIG. 3 graphs the top-hat light distribution compared to the Gaussian light distribution.

Figure 4:
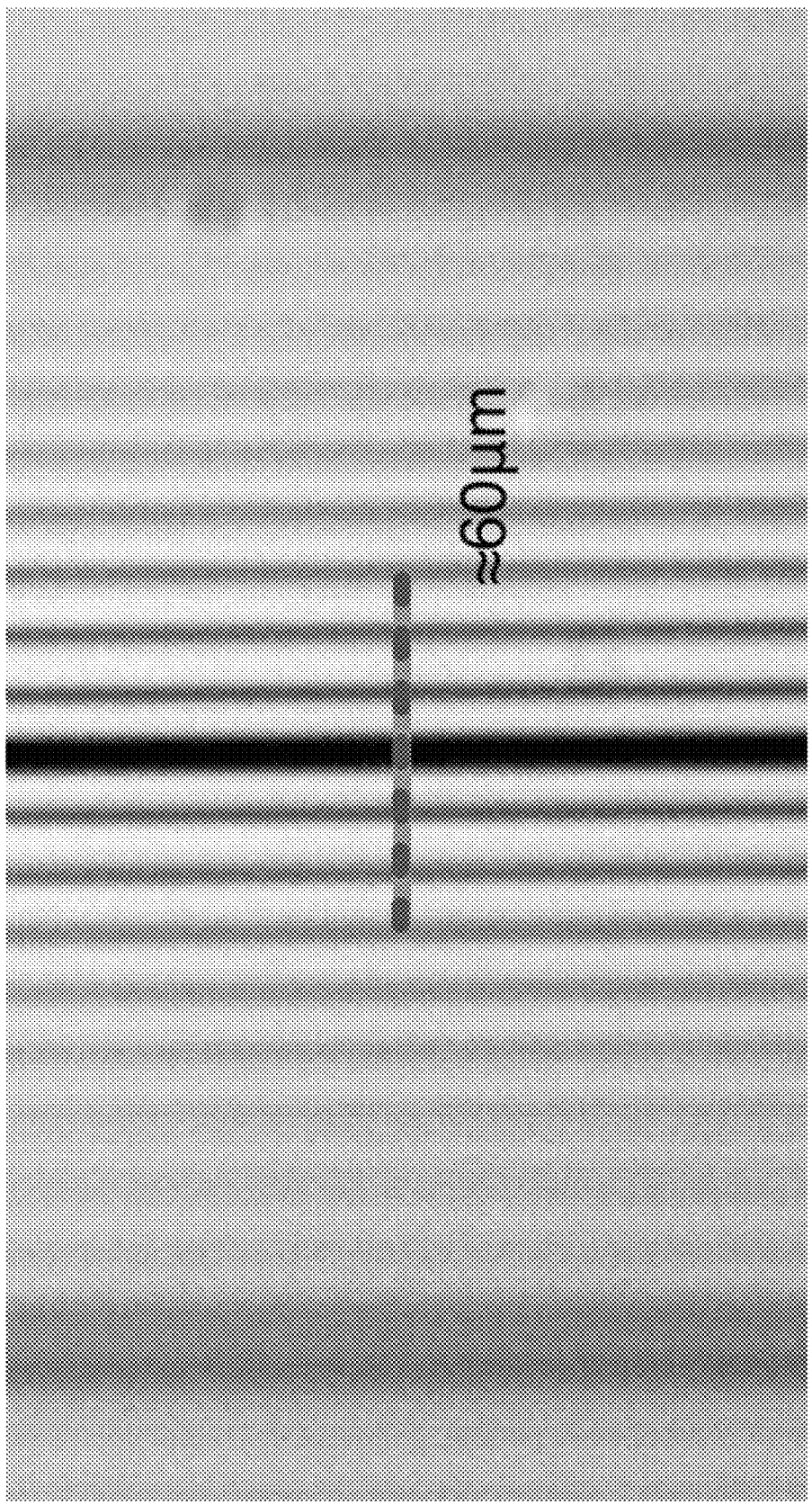

FIG. 4 illustrates a microscale grating for sensor calibration, in particular to determine depth of field (placed at 45-degree angle to the line of observation).

FIG. 5 presents a table of sample dilutions for polystyrene size standards.

Figure 6:
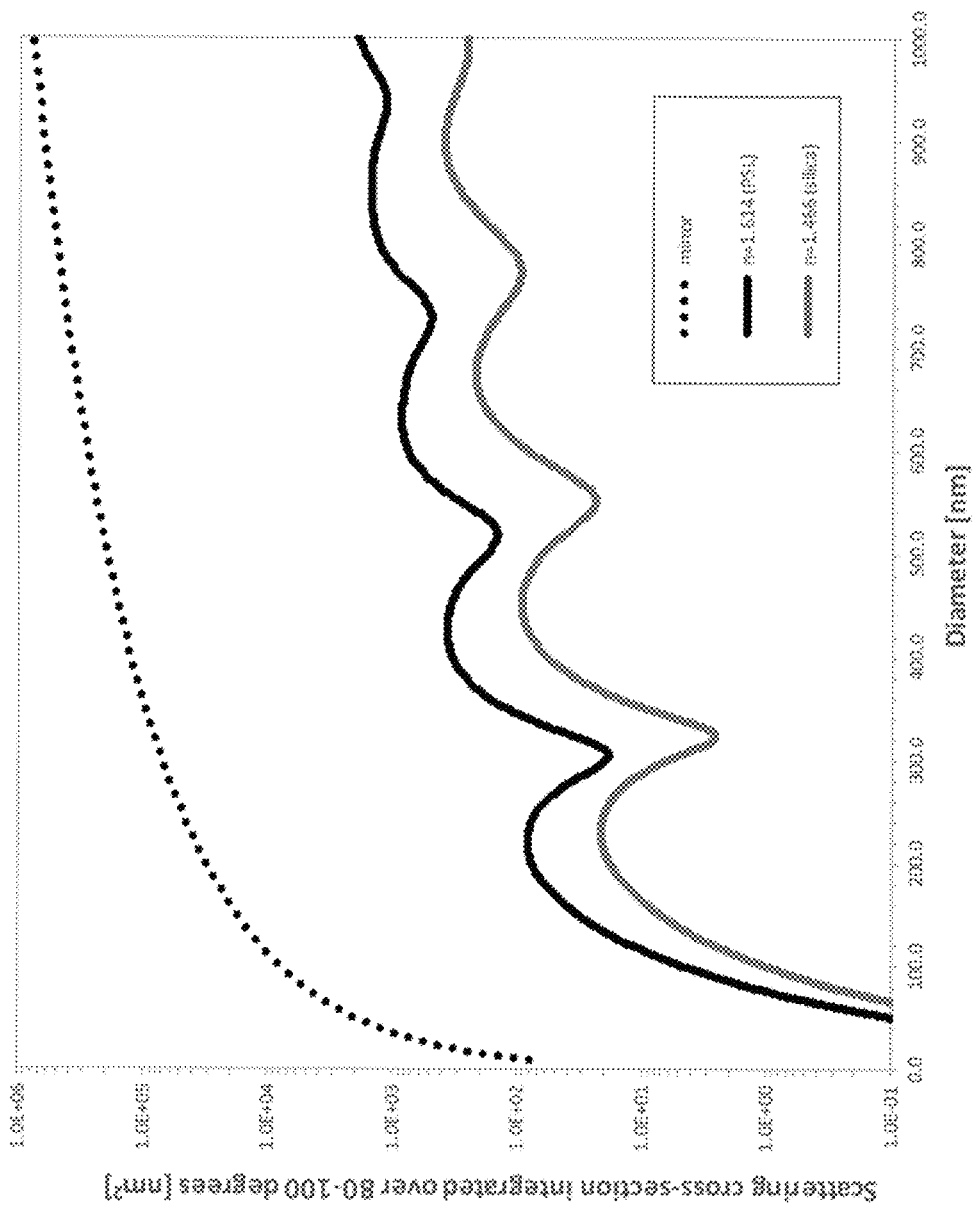

FIG. 6 presents the Mie scattering cross sections calculated for polystyrene and silica in water.

Figure 7A:
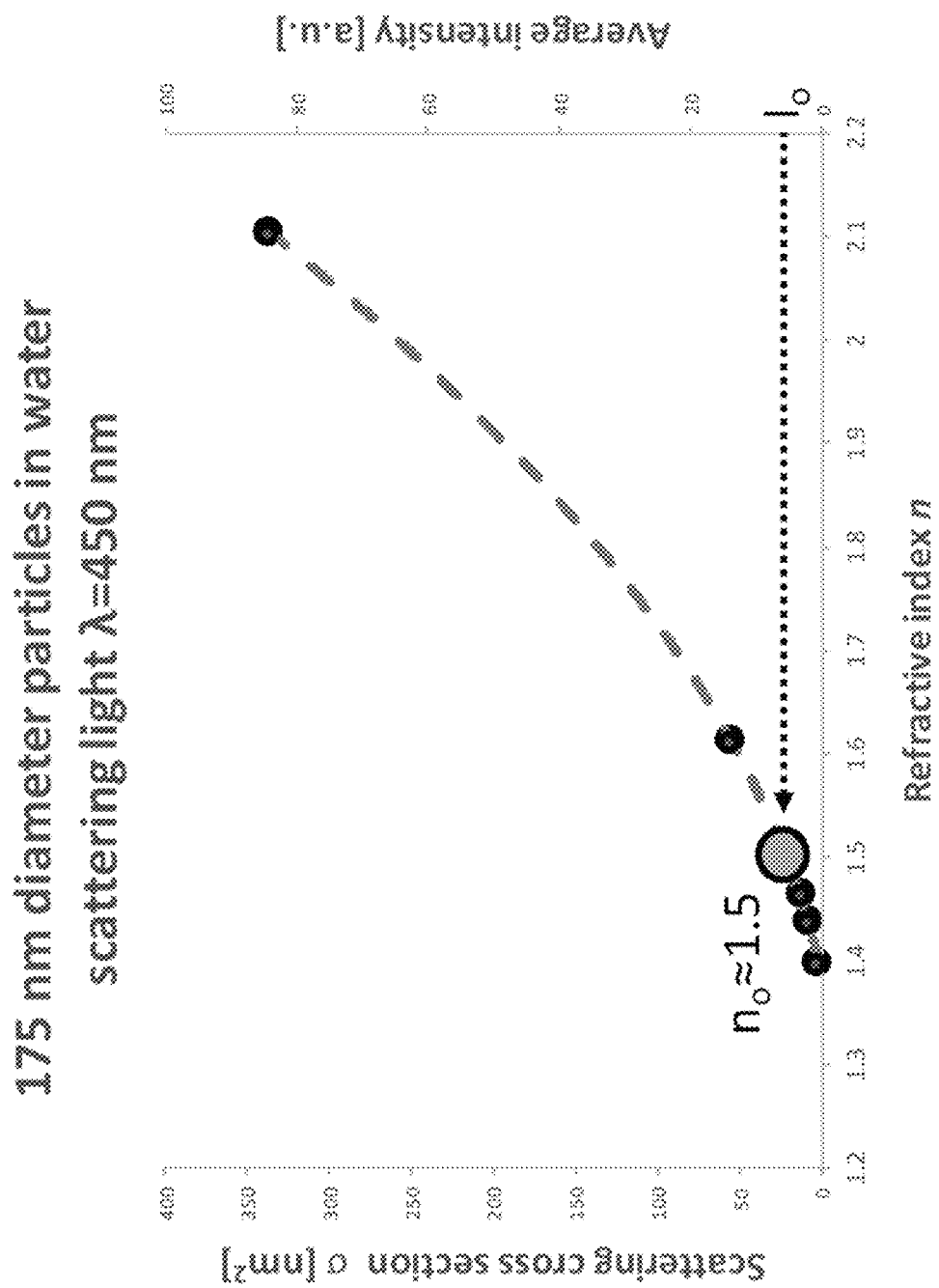

FIG. 7A is a graph of observed average intensity plotted against the refractive index for particles of 175 nm diameter in water with a light source wavelength of 450 nm.

Figure 7B:
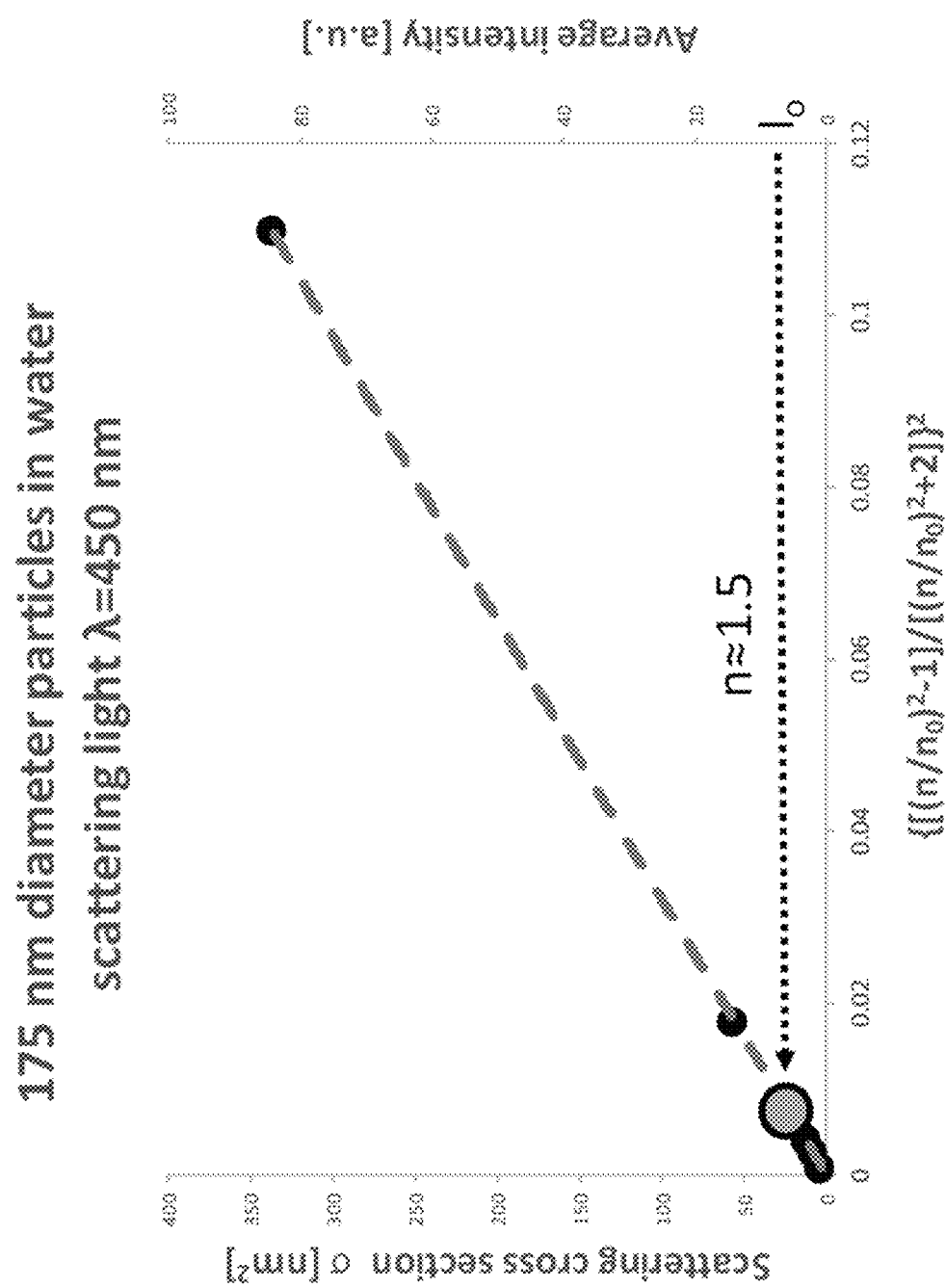

FIG. 7B is a graph of observed average intensity plotted against the refractive index for particles of 175 nm diameter in water with a light source wavelength of 450 nm, where the horizontal axis has been changed to the Rayleigh scattering proportionality parameter.

Figure 7C:
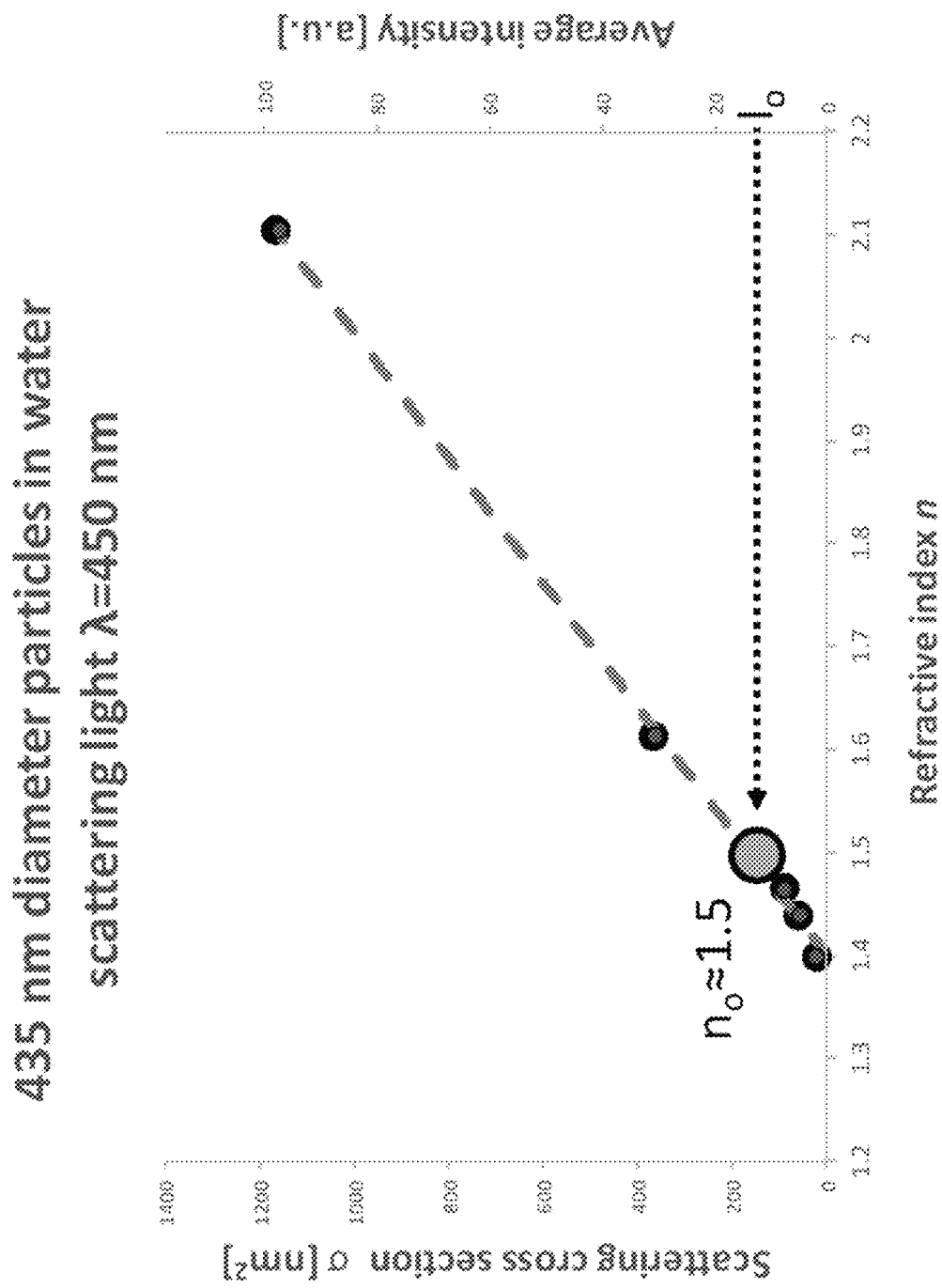

FIG. 7C is a graph of observed average intensity plotted against the refractive index for particles of 435 nm diameter in water with a light source wavelength of 450 nm.

Figure 8A:
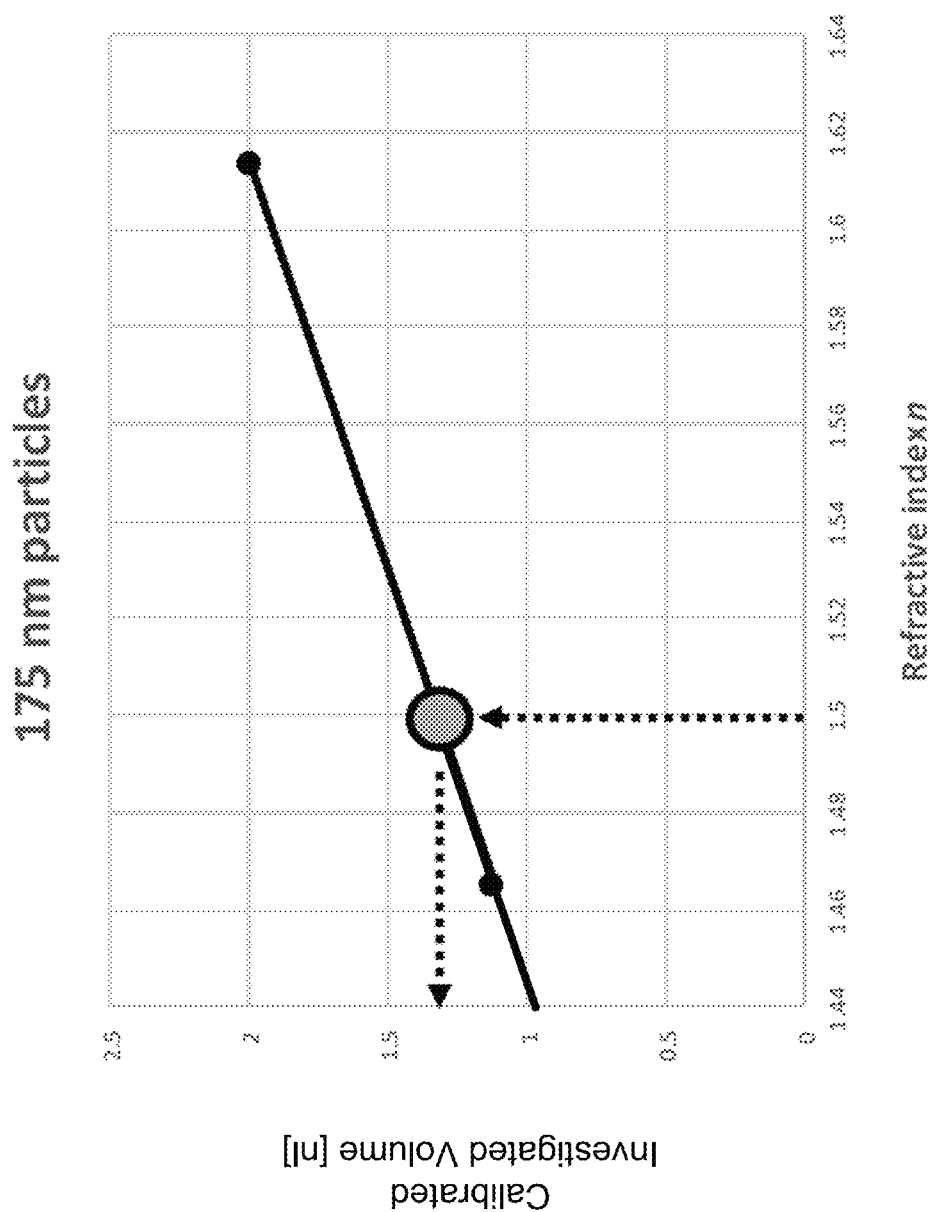

FIG. 8A is a graph of calibrated investigated volume plotted against the refractive index for particles of 175 nm diameter in water with a light source wavelength of 450 nm.

Figure 8B:
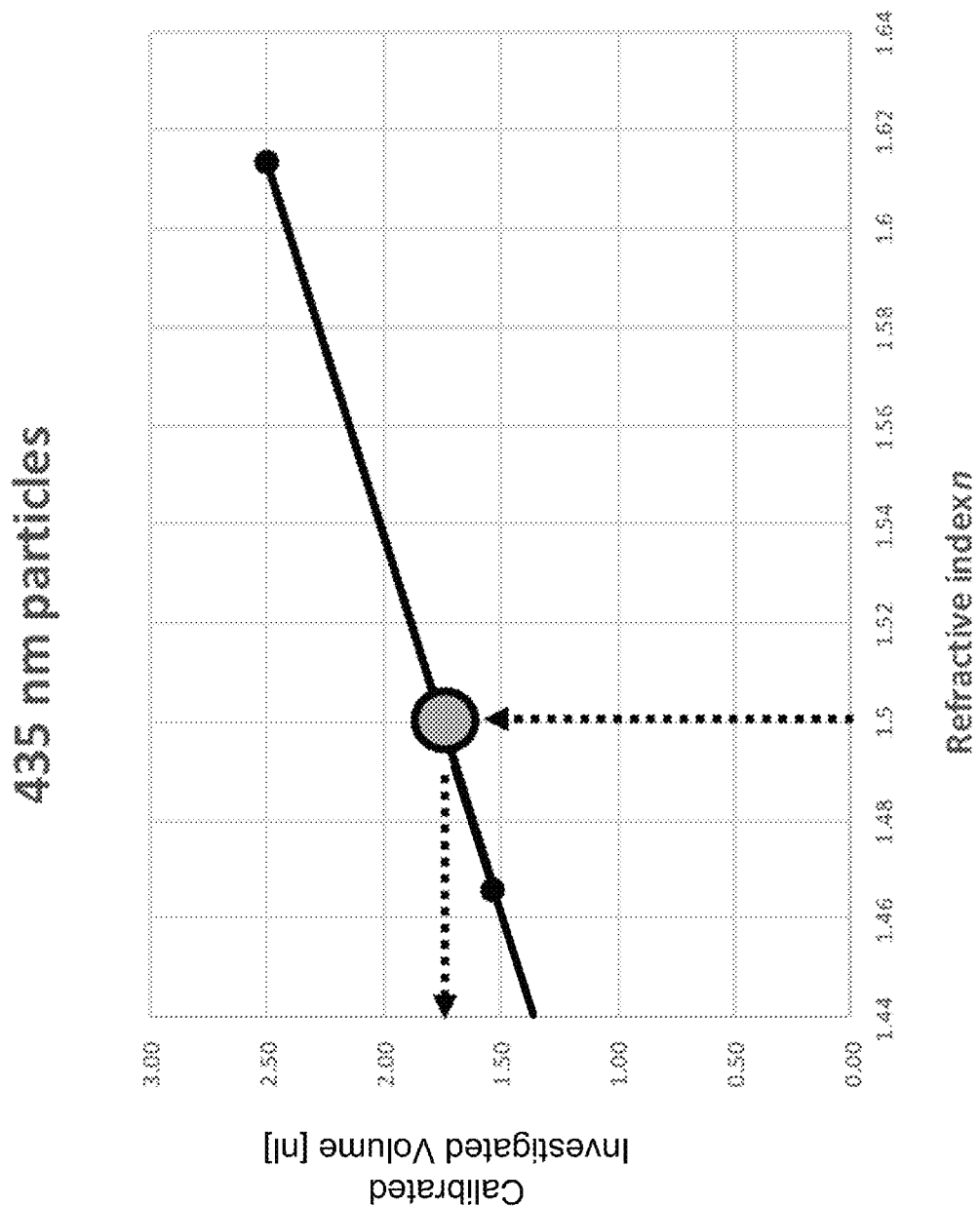

FIG. 8B is a graph of calibrated investigated volume plotted against the refractive index for particles of 435 nm diameter in water with a light source wavelength of 450 nm.

Figure 9:
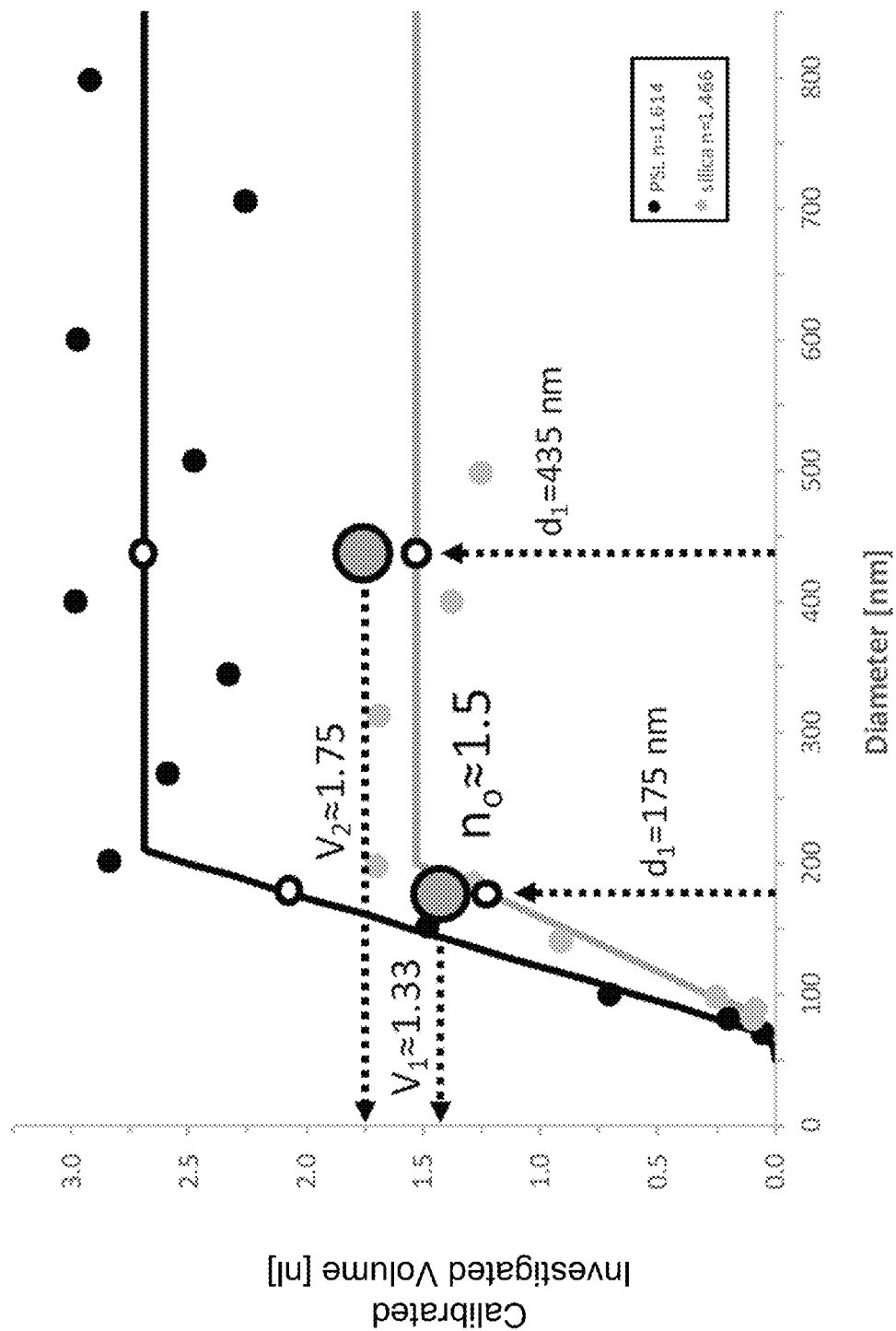

FIG. 9 shows schematically a composite presentation for two different sizes of (unknown) particles $d_1$ and $d_2$ (large circles) in water with resulting different calibrated investigated volumes V1 and V2, respectively.

Figure 10:
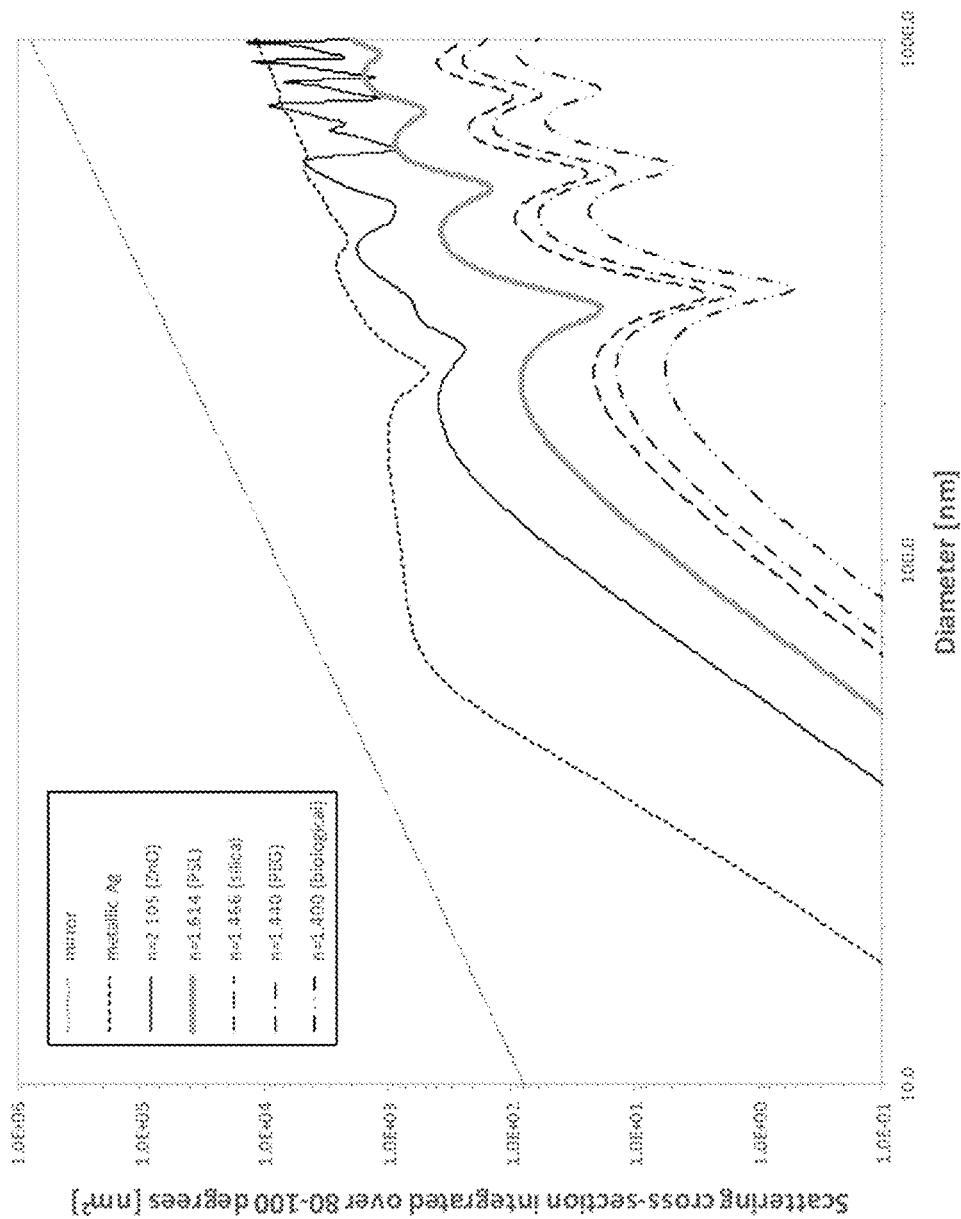

FIG. 10 shows the Mie scattering cross sections calculated for materials of various refractive indices in water.

Figure 11:
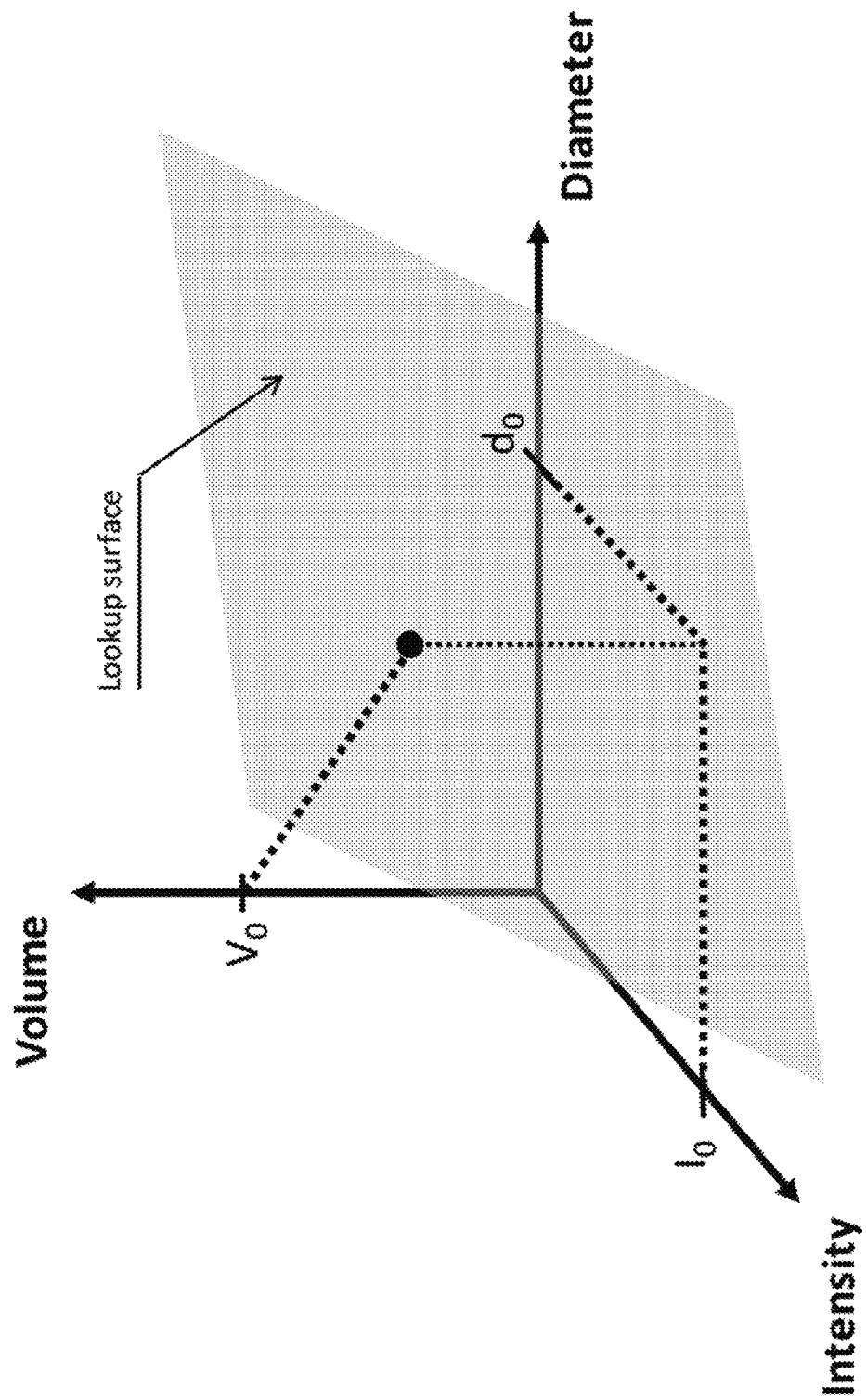

FIG. 11 shows schematically a three-dimensional graph that yields an investigated volume lookup surface for a given diluent.

Figure 12:
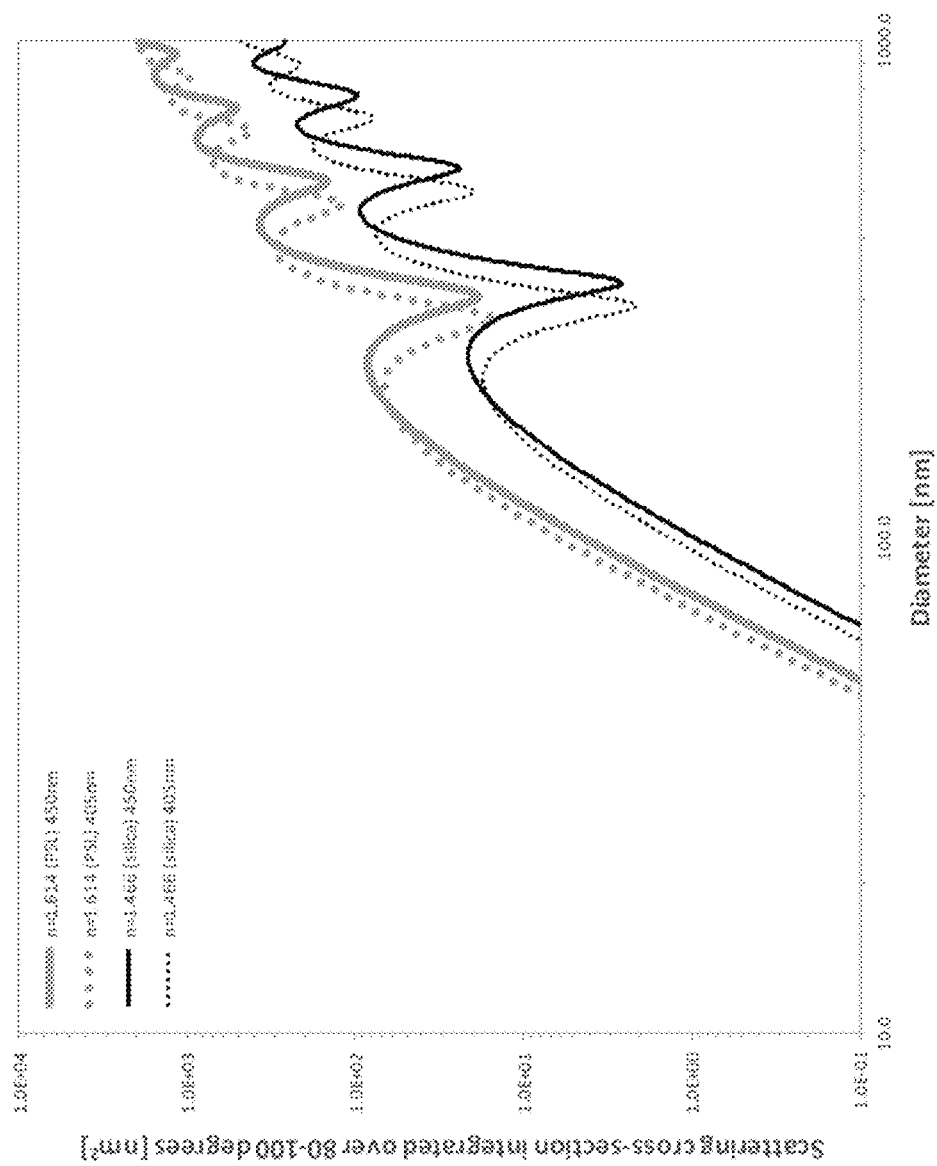

FIG. 12 shows a comparison of the Mie scattering cross sections calculated for polystyrene and silica in water at two different wavelengths.

Figure 13:
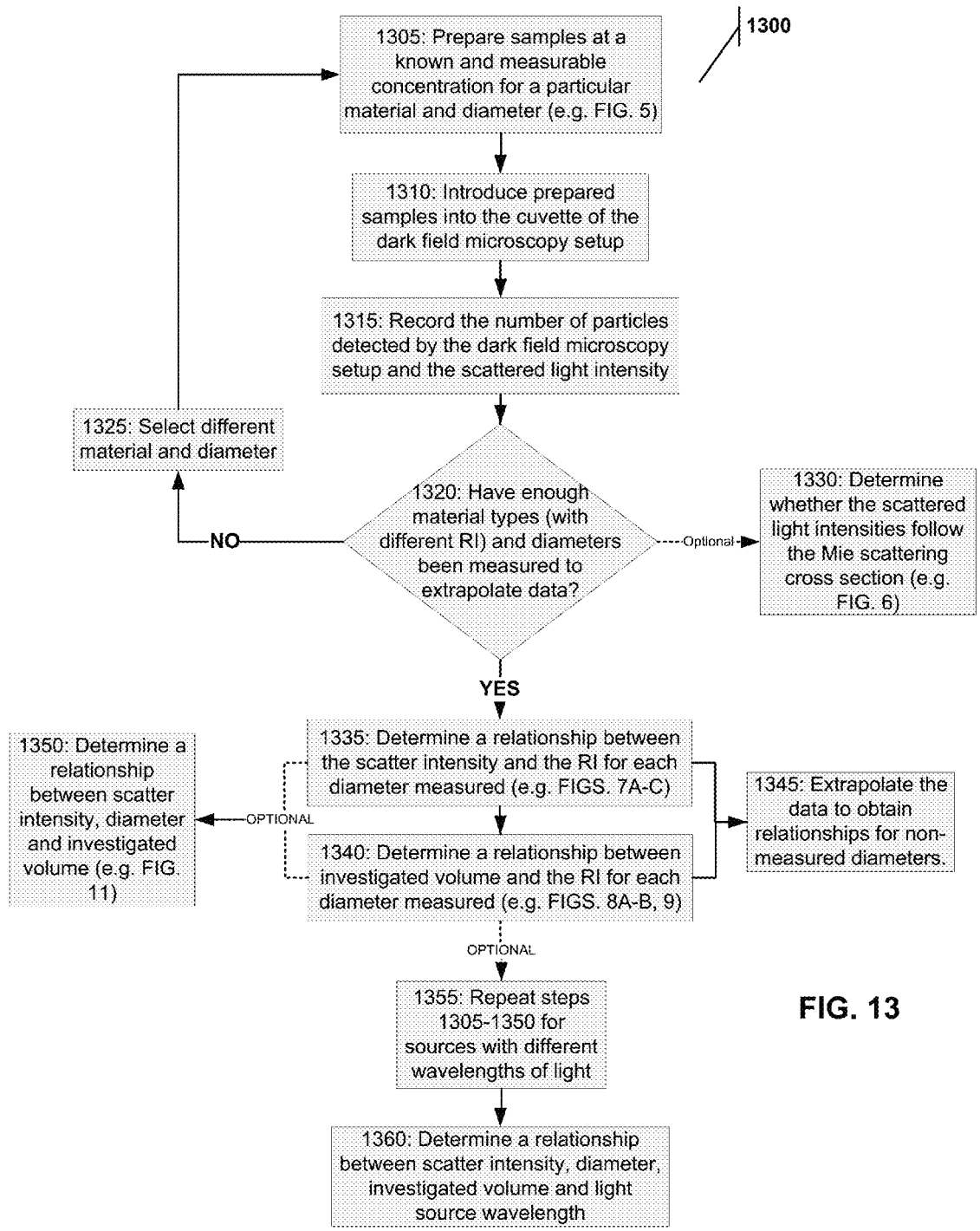

FIG. 13 is a flowchart illustrating the method to estimate the effective thickness of light sheet that can be used to precisely calculate a concentration of tracked and counted particles.

Figure 14:
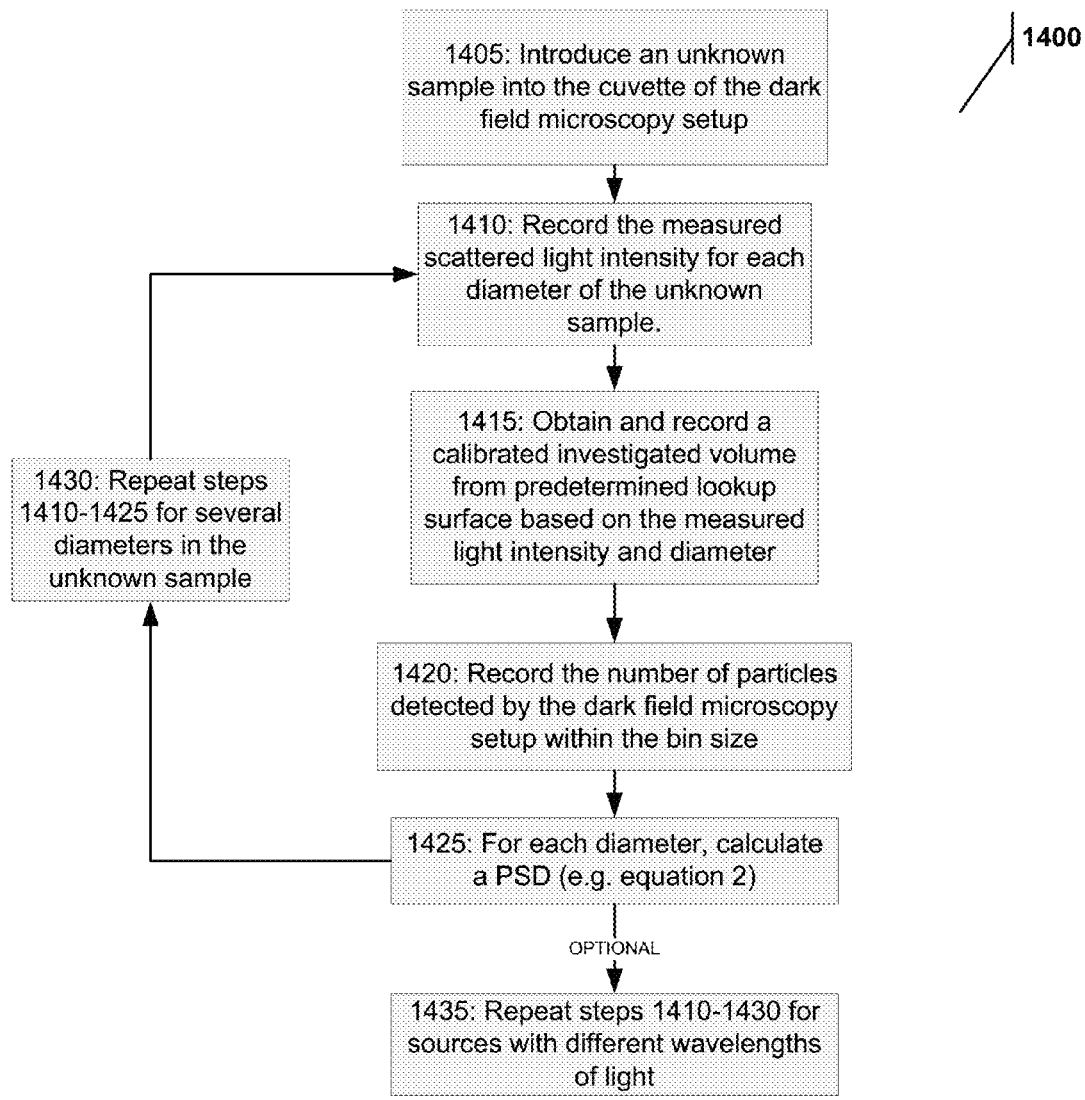

FIG. 14 is a flowchart illustrating the method for using the calibrated investigated volume to obtain particle size distribution for an unknown poly-disperse sample in a known diluent.

Figure 15:
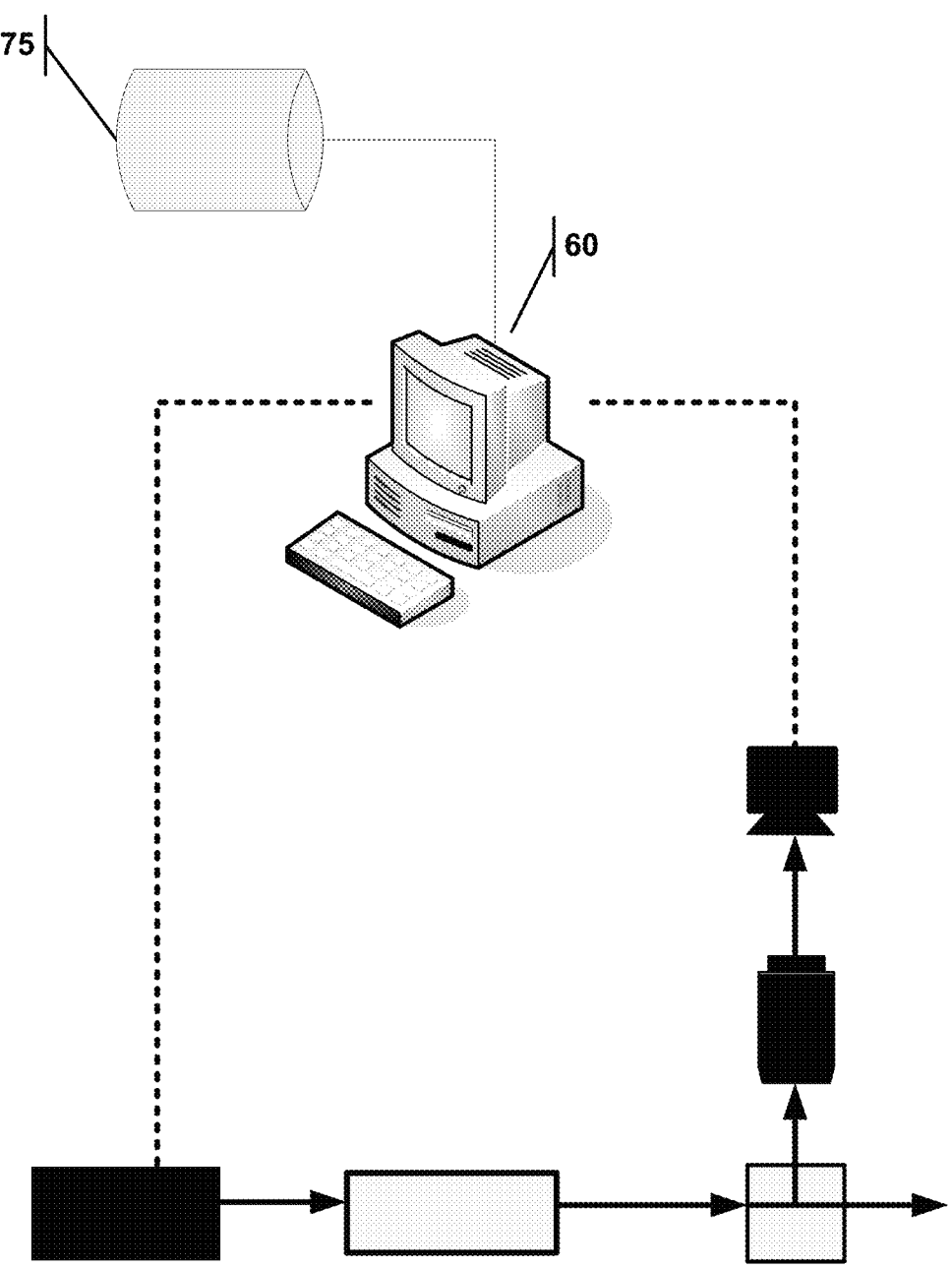

FIG. 15 is a dark field microscopy setup with a database containing the predetermined relationships.

6.0 DETAILED DESCRIPTION

Reference is made herein to some specific examples of the present invention, including any best modes contemplated by the inventor for carrying out the invention. Examples of these specific embodiments are illustrated in the accompanying figures. While the invention is described in conjunction with these specific embodiments, it will be understood that it is not intended to limit the invention to the described or illustrated embodiments. To the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, process operations well known to persons of skill in the art have not been described in detail in order not to obscure unnecessarily the present invention. Various techniques and mechanisms of the present invention will sometimes be described in singular form for clarity. However, it should be noted that some embodiments include multiple iterations of a technique or multiple mechanisms unless noted otherwise. Similarly, various steps of the methods shown and described herein are not necessarily performed in the order indicated, or performed at all in certain embodiments. Accordingly, some implementations of the methods discussed herein may include more or fewer steps than those shown or described. Further, the techniques and mechanisms of the present invention will sometimes describe a connection, relationship or communication between two or more entities. It should be noted that a connection or relationship between entities does not necessarily mean a direct, unimpeded connection, as a variety of other entities or processes may reside or occur between any two entities. Consequently, an indicated connection does not necessarily mean a direct, unimpeded connection unless otherwise noted.

The following list of example features corresponds with FIGS. 1-15 and is provided for ease of reference, where like reference numerals designate corresponding features throughout the specification and figures:

instrument setup 10
light source 15
light beam 20
optical objective 25
light sheet 30
small cell, specimen chamber, (cuvette) 35
investigated volume 38
scattered light 40
focusing optical objective 45
focused light beam 50
sensor (e.g., camera) 55
processor 60
"top hat" light intensity characteristic 65
Gaussian-like profile 70
Database 75

Method to estimate the effective thickness of light sheet that can be used to precisely calculate concentrations of tracked and counted particles 1300 (comprised of steps 1305-1360).

Method for using the calibrated investigated volume to obtain particle size distribution for unknown poly-disperse sample 1400 (comprised of steps 1405-1435).

Figure 1A:
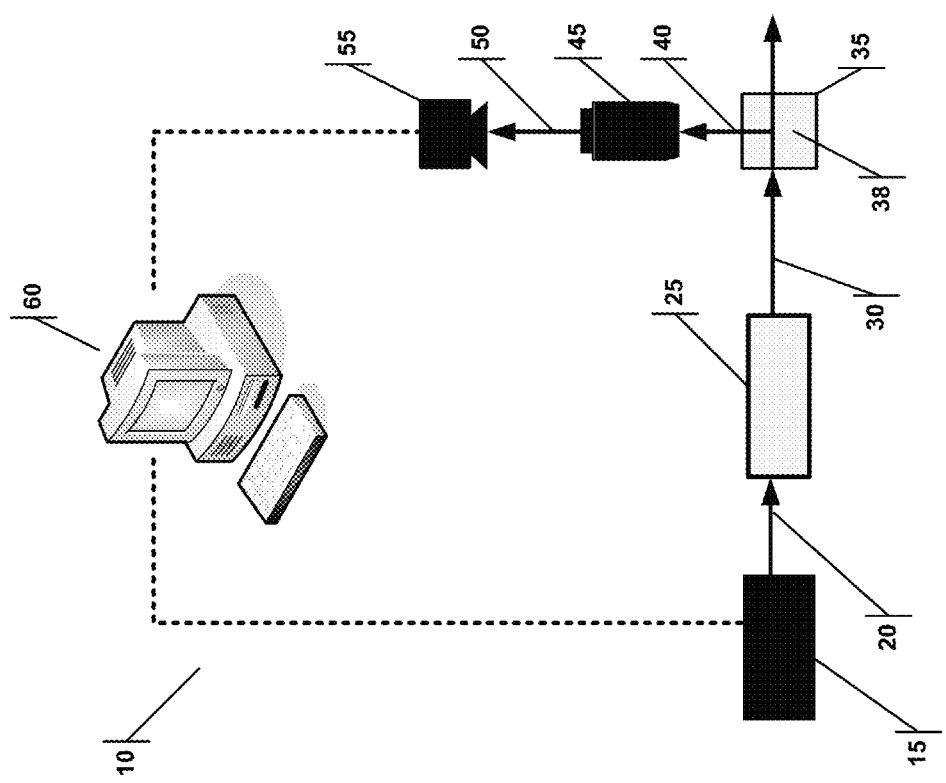
FIG. 1A illustrates a dark field microscopy setup.
Figure 1B:
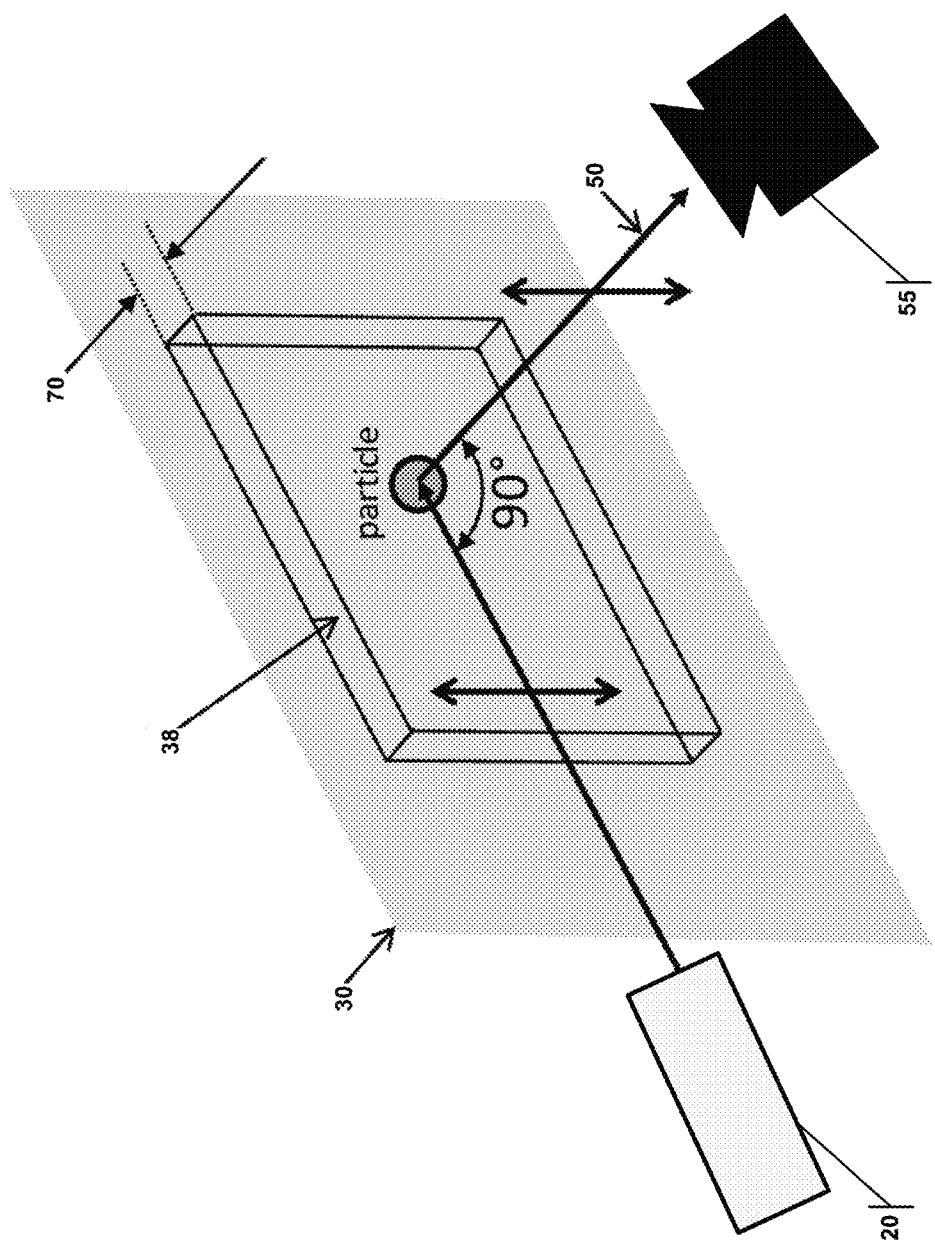
FIG. 1B illustrates a portion of the dark field microscopy setup, detailing the investigative volume and polarizations of entering and scattered light.
Figure 2:
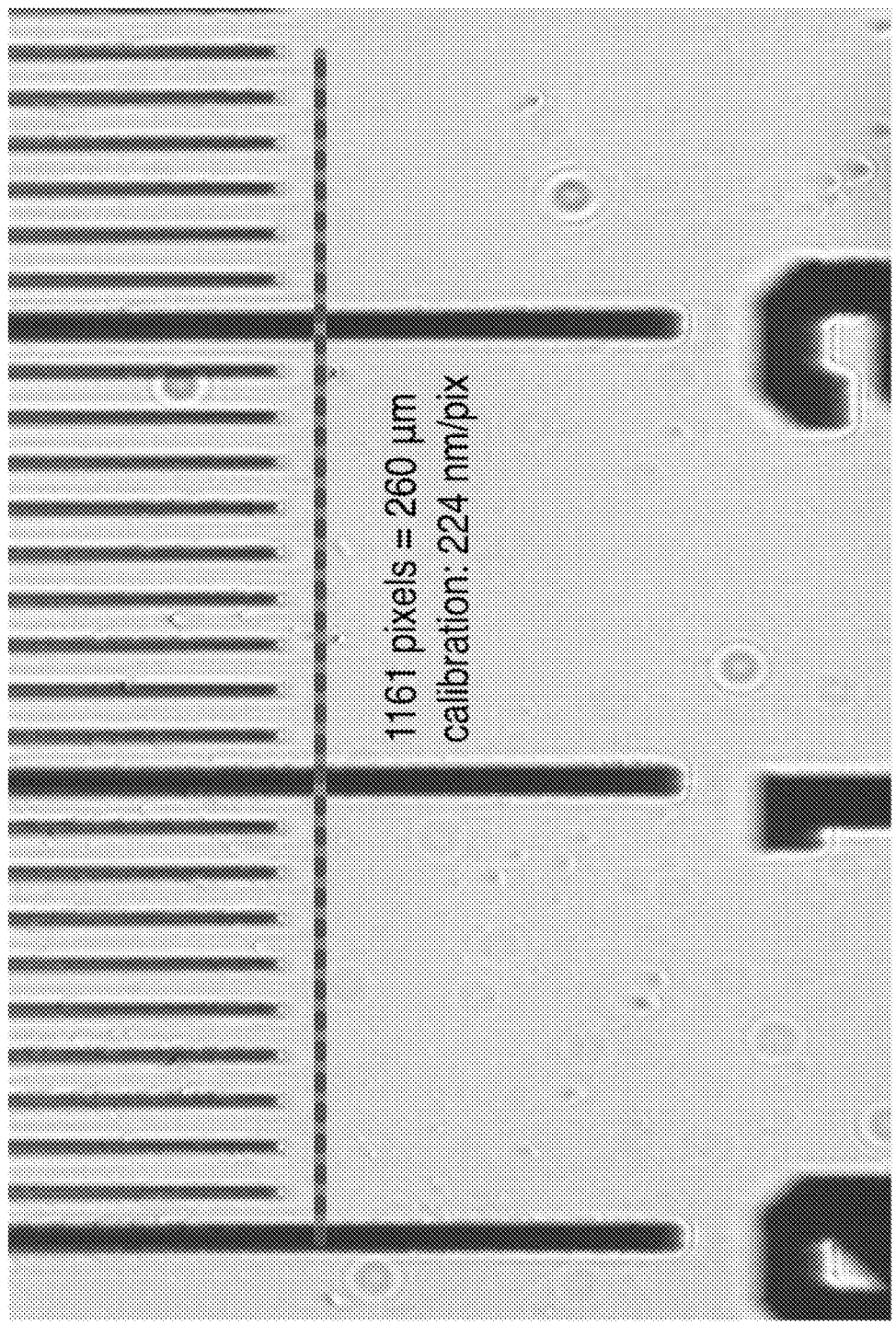
FIG. 2 illustrates a microscale grating for sensor calibration.

The schematic of light sheet 30 that allows visualization described herein is depicted in FIG. 1A. It comprises of a light source 15 (a laser or multiple lasers with different beam color/wavelength that can pass through an optical objective or other beam forming elements 25) that creates a very narrow light sheet 30 inside a transparent cuvette 35 (also known as a specimen chamber). Light scattered 40 by particles illuminated in a given colloid contained in the cuvette 35 is typically being observed at 90-degree angle by a microscope (objective) 45 that collects light on a sensor 55 (digital video camera). Because typical size of nanoparticles (diameter below 1 micron) is comparable with the wavelength of visible light, the microscope 45 is not able to distinguish details of light scattering nanoparticles but records only the intensity of light scattered by each particle, projecting an image that looks like a circular blob or disc that covers several pixels on the sensor 55. To calibrate the area of light sheet 30 observed by the sensor 55 an image of microscale gratings is placed in front of the objective 45 instead of a cuvette 30; such a microscale grating is shown in FIG. 2. In this example, 1161 pixels in a sensor image cover distance of 260 microns, hence calibration constant is about 224 nm per pixel. For 1280-pixel by 720-pixel image depicted here, the area is 46,242 square micrometers or 0.000462 $cm^2$. Typical digital sensors have square pixels, hence calibration is uniform in any direction but if rectangular pixels are used then the same procedure can be applied in each perpendicular direction along rows of pixels.

To calculate the volume from which particles scattering light are contributing to the images recorded by the apparatus, the depth of field (DOF) of the optical system must be considered and should be large enough to cover the whole thickness of the light sheet 30. FIG. 4 shows an image of the same microscale grating used to calibrate the system but this time the grating is rotated 45 degrees off the optical axis. Precise determination of the limits of sharp images vs. fuzzy ones is subjective but it is obvious that in this example such a distance is in the range of tens of microns (approximately 60 microns). Taking into account rotation of a microscale (factor of √2 shorter distance along optical axis) as well as the fact that tracking and counting is done inside a cuvette filled with a diluent (in case of water, the most popular diluent, whose refractive index in respect to air is about 1.33, this is an elongation by the factor of about 4/3 vs. apparent perceived depth), in the example shown in FIG. 4, the effective DOF of the system is estimated to be approximately 56 microns. In the case of a rationally designed instrument, this DOF would necessitate creation of light sheet that should have average thickness of about or less than 56 microns as well. In the above-mentioned example of sensor 55 equipped with 20× enlarging objective 45, the investigated volume would be about 2.6 million cubic microns or about 2.6 nL.

To efficiently detect, track and count particles in a given colloid by the method described in this patent, the number of particle images visible within each frame of recorded video should be limited because with too many particles present there is increased probability that tracks will eventually overlap during typical run of few hundred frames thus precluding exact tracking. Typical number of particles that still can be detected and tracked in the described embodiment is about 250, thus limiting useful concentration/density of examined samples to below about $10^8$ particles/mL.

FIG. 13 illustrates a method 1300 of estimating the effective thickness of light sheet that can be used to precisely calculate a concentration of tracked and counted particles.

To begin the calibration, a colloid sample in a known diluent with a known particle density should be prepared and used (step 1305). As mentioned above, tracking of particle becomes more difficult and even impossible when there are too many particles in the video image. Therefore, a useful concentration concentration/density is below $10^8$ particles/mL. Because particles of different sizes absorb and reflect light differently, several particle diameters of known concentrations/densities should be used. The tested samples should have known concentrations of particles, which may be obtained e.g. by the gravimetric method. Typically, sizing standards contain 1% per weight of particles. This allows for precise estimate of the concentration obtained by subsequent dilutions of such standards that are needed to reach useful concentrations. The table presented in FIG. 5 provides sample dilutions to arrive at a particle density of about $2 \times 10^7$ particles/mL of polystyrene (PSL) particles of various sizes in a very clean water obtained from the Millipore Corporation.

These samples are then introduced into the cuvette 35 of the dark field microscopy setup 10 at step 1310 (i.e. see the set up in FIGS. 1A and 1B), and the number of particles detected by the setup 10 is recorded and compared to the number known from the dilution (i.e., the table in FIG. 5). This data will be used to create a volumetric calibration. The calculated average scattered light intensity for various particles diameters in a known diluent is also recorded for standard, fixed laser powers and camera gains used in setup 10 (step 1315).

In a preferred embodiment, the preparation of known dilutions with different particle diameters should be repeated for materials with different refractive indices (e.g. silica, polystyrene and gold) in different diluents, and the measured particle concentration should be compared to the known concentration for each material (1325) sufficient to extrapolate material types (i.e., different refractive indices relative to a diluent) and diameters (step 1320). The number of samples should be at least for two different materials, at least two different diluents and at least two different diameters, but optimally it is more than three materials, several diluents and many diameters covering the range of interest (e.g. below 1000 nm and down to 10 nm as well as materials with RI ranging from 1.4 to 2.0). Likewise, the average scattered light intensity for various particles diameters (for each material of a different relative refractive index, vs. RI of diluent average being calculated between many tracks of same size particles observed in same diluents) is also recorded for standard, fixed laser powers and camera gains used in setup 10. This can be repeated for other laser power settings and camera gains or extrapolated knowing ratios of powers and gains for those settings.

It is further advantageous to check if the results for scattered light intensity follow Mie scattering cross section calculated for known relative refractive indices (step 1330). (See FIG. 6 for comparison of scattering cross section for PSL and silica nanoparticles in water, cf. reference van der Pol et al (2014) "*Refractive index determination of nanoparticles in suspension using NTA*").

At step 1335, for each size particle, the relative refractive index is plotted against the average measured intensity as shown in FIG. 7A (175 nm diameter particles in water with a light source wavelength of 450 nm). For particles smaller than about 200 nm diameter, the scattering cross sections and observed intensities are linear with the Rayleigh scattering proportionality parameter (n being refractive index of scattering material, $n_0$ refractive index of a diluent):

$$\left[ \frac{\left(\frac{n}{n_0}\right)^2 - 1}{\left(\frac{n}{n_0}\right)^2 + 2} \right]^2 \qquad \text{Equation 1}$$

FIG. 7B shows the same data in FIG. 7A, however the horizontal axis is derived from Equation 1, yielding a linear relationship. For particles larger than 200 nm diameter, the light intensity shares a linear relationship with the refractive index n of particles, as shown in FIG. 7C (435 nm diameter particles in water with a light source wavelength of 450 nm).

The main point of the method is to provide a calibration method to account for the fact that the investigated volume is not constant for particles of different sizes in different diluents because different sized particles will scatter light differently, likewise for particles with different refractive indexes vs. refractive indices of diluents. Without proper calibration of the investigated volume, the number of particles that are observed and counted will be a misrepresentation of the actual number of particles within the colloid.

In FIG. 8A, a series of 175 nm diameter particles in water of different refractive indices are measured and counted, and the refractive index is plotted against the investigated volume (step 1340). The investigated volume from FIG. 8A is the calibration factor that will correct the over/undercounting of particles of different sizes and different relative refractive index. FIG. 8A is dependent on the setup as well as on the wavelength of the light source that is used. The user could create the graphs (i.e., FIGS. 7A-8B) for the particular setup and light source, and test unknown samples using the same setup and source.

The calibrated investigated volume is determined by a comparison of the number of known particles in the investigated volume as compared to the observed number of particles. So, if for one refractive index twice as many particles are observed than for particles with a lower refractive index but the same concentration in same liquid, then the calibrated investigated volume of the first should be twice that of the second. Turning to FIG. 8A again, lower refractive index particles tend to scatter light less efficiently, so the calibrated investigated volume will be close to 1 nL, while the higher refractive index particles scatter light more efficiently and the calibrated volume will be close to 2 nL. When the particle size distribution (PSD) is being calculated, the equation used to sum all particles belonging in i-th bin (their number being j) is:

$$PSD(i) = \frac{1}{d_i} \sum_j \frac{1}{V_j} \qquad \text{Equation 2}$$

where $d_i$ is the width of i-th bin and summation is over all j particles binned and each having calibrated investigated volumes $V_j$ determined individually as described above.

Therefore, the number of particles made from the high refractive index material will be discounted by the larger calibrated investigated volume. Indeed, FIG. 8A starkly illustrates the problem with uncalibrated investigated volumes. Without calibration, a 175 nm diameter particle with a refractive index of 1.45 would have been undercounted by about 50% as compared to the same sized particles with a refractive index of 1.61, both placed in water. FIG. 8B creates the same graph, and demonstrates similar effects, for 435 nm diameter particle in water.

FIG. 9 shows schematically a composite presentation of this process for two different sizes of (unknown) particles $d_1$ and $d_2$ (large circles) in water with resulting different calibrated volumes $V_1$ and $V_2$, respectively.

While the graphs shown in FIGS. 7A-9 were created using discrete types of materials, the results can be extrapolated beyond the tested particles (for wider range of refractive indices, particle sizes or different diluents) by performing Mie calculations of scattering cross sections for the geometry of apparatus being calibrated (namely for the numerical aperture NA of the objective used). For example, FIG. 10 provides the Mie calculations for various materials, water being the diluent ($n_0$=1.33).

The information in FIG. 7A-9, can be combined into a three-dimensional surface graph shown in FIG. 11 (optional step 1350). The system can measure the light intensity and the diameter of the particle in a given diluent and therefore can determine the calibrated investigated volume by resorting to the look-up surface for that diluent. Once the calibrated investigated volume is determined, then the system counts the number of particles in the particular bin size and applies equation 2 above, with the calibrated investigated volumes for each particle with size corresponding to that bin.

In steps 1355 and 1360, the look-up surface shown in FIG. 11 is made more robust by including extrapolations that include differing wavelength of the source light. So, for example, FIG. 12, shows the Mie calculations for polystyrene (PSL) and silica scattering cross-sections in water for 405 nm and 450 nm light wavelengths, respectively. This would result in a four-dimensional matrix, which is not easy to graph in 2D, but is essentially the surface of FIG. 11 with an additional axis of light source wavelength in fourth dimension. Such a matrix could be created and calculated by a computer processor. The system would use the wavelength, diameter and intensity to extrapolate the calibrated investigated volume for each particle. And from those calibrated volumes, an accurate PSD can be calculated. Yet another dimension is added by considering various diluents in the procedure described above.

As shown in FIG. 14, a method 1400 for using the calibrated investigated volume to obtain particle size distribution for unknown poly-disperse sample is disclosed. An unknown poly-disperse sample in a known diluent is loaded into the cuvette (Step 1405) and the source light wavelength is set. The measured scatter intensity of the unknown particles is recorded as is the diameter at step 1410. Those two values are then used to determine the calibrated investigated volume from the lookup surface FIG. 12 (Step 1415) for a given diluent—or if the surface is not used, obtaining the calibrated investigated volume by the graphs discussed above in relation to FIGS. 7A-9. The number of particles in the particular bin size is also recorded at step 1420. Applying equation 2 above, with the calculated investigated volumes for each particle, the PSD for the sample can be calculated at step 1425. This process can be repeated for several diameters in the unknown sample in a known diluent (step 1430), and for various wavelengths (step 1435).

The method 1400 may be implemented on a processor 60 as shown in FIG. 15. Specifically, the predetermined relationship between the scattered light intensity and the sample's relative refractive index vs. diluent, as well as the predetermined relationship between the investigated volume and the sample's relative refractive index, may be part of the processor's database 75. The processor 60 can record the measured scatter intensity by the unknown particles in a known diluent, the particle size and the number of particles. Based on this information, the processor can determine the calibrated investigated volumes for all particles counted and create a PSD for the unknown sample. If multiple wavelengths of light are used, the processor can use the light source wavelength and can perform these determinations from the database, which may have the scattered light intensity vs. refractive index and the calibrated investigated volume vs. refractive index relationships based on various wavelengths.

Now that a robust method for determining a calibrated investigative volume has been described, it should be noted that these same techniques may be used to determine a calibrated investigative volume for a homogenous colloid (when particles' material is considered). Referring to FIG. 9, the top line charts the diameter of a particle to the calibrated investigative volume for silica with a refractive index of 1.466. If the homogenous but unknown material's sample has particles in the same diluent that have a similar scattering intensity over the particle diameters as that of silica (see e.g., FIGS. 7A-7C), then it has a similar refractive index of silica vs. that diluent; thus the silica calibrated investigative volumes for that diluent may be used (i.e., FIG. 9). This is in essence a single curve (section) of the 3-D surface shown in FIG. 11. This is a simplified case that does not require multiple samples of known sizes and refractive indices relative to diluent to arrive at the calibrated investigative volume.

Although exemplary embodiments and applications of the invention have been described herein including as described above and shown in the included example Figures, there is no intention that the invention be limited to these exemplary embodiments and applications or to the manner in which the exemplary embodiments and applications operate or are described herein. Indeed, many variations and modifications to the exemplary embodiments are possible as would be apparent to a person of ordinary skill in the art. The invention may include any device, structure, method, or functionality, as long as the resulting device, system or method falls within the scope of one of the claims that are allowed by the patent office based on this or any related patent application.

The invention claimed is:

1. A system for determining the particle size distribution of a colloid, the system comprising:
   a light source constructed to emit a beam of electromagnetic radiation at a specimen chamber, the chamber is constructed to hold the colloid and to allow a portion of the beam to scatter from particles contained in the colloid;
   a sensor positioned to observe the scattered portion of the beam, wherein the sensor is adapted to detect the electromagnetic radiation;
   a database configured to store a predetermined relationship between a scattered light intensity, a particle size and a calibrated investigated volume;
   a processor connected to the light source, sensor and the database, the processor configured to perform the following steps:
   a. activating the light source;
   b. obtaining a series of images from the sensor;
   c. determining the size of the particles in the images by tracking Brownian motion, for each size;
      i. measuring the number of particles in the images;
      ii. measuring the scattered light intensity for the particles in the images individually;
      iii. based on steps (c)(i) and (ii), determining the calibrated investigated volume base on the predetermined relationship;
   d. calculating the particle size distribution of the colloid based on the measured number of particles from step (c)(i) and the determined calibrated investigated volume from step (c)(iii).

2. The system of claim 1, wherein the predetermined relationship is further dependent on the wavelength of the electromagnetic radiation; wherein the light sources can be adjusted to produce electromagnetic radiation at a plurality of wavelengths; and wherein the processor is further configured to adjust the light source to produce a plurality of wavelengths.

3. A method for calibrating dark field microcopy setup, wherein the setup comprises a light source constructed to emit a beam of electromagnetic radiation at a specimen chamber, the chamber is constructed to hold the colloidal particles and to allow a portion of the beam to scatter from the particles, the scattered portion of the beam directed to a sensor, wherein the sensor is adapted to detect the electromagnetic radiation, the method comprising:
   a. preparing a plurality of particle samples with known concentrations and particle sizes, the plurality having more than one refractive index and more than one particle size;
   b. for each sample in the plurality:
      i. introducing the sample into the specimen chamber;
      ii. activating the light source;
      iii. measuring a scattered light intensity and a number of particles detected by the sensor;
   c. determining a relationship between the scattered light intensity and the sample's refractive index for each particle size in the plurality;
   d. determining a relationship between an investigated volume and the sample's refractive index for each particle size in the plurality, based on the number of particles measured for the sample, and
   e. determining calibrated investigated volumes based on the relationships of steps (c) and (d).

4. The method of claim 3, further comprising: determining a three-dimensional relationship between the scattered light intensity, particle size and investigated volume.

5. The method of claim 3, further comprising: based on the determination of step (c), determining a relationship between the scattered light intensity and refractive index for particle sizes not measured in the plurality.

6. The method of claim 3, further comprising: based on the determination of step (d), determining a relationship between the investigated volume and refractive index for particle sizes not measured in the plurality.

7. The method of claim 3, wherein the light source is altered to produce electromagnetic radiation at a plurality of wavelengths, the method further comprising; performing steps (a)-(d) for each wavelength in the plurality.

8. The method of claim 7, further comprising: determining a four-dimensional relationship between the light source wavelength, the scattered light intensity, particle size and investigated volume.

9. The method of claim 3, further comprising:
   introducing an unknown sample into the specimen chamber;
   activating the light source;
   for the plurality of particle sizes in the unknown sample:
      i. measuring the scattered light intensity and a number of particles detected by the sensor;
      ii. calculating a particle size distribution based on the calibrated investigated volumes and the measured number of particles from the unknown sample.

10. A method for calibrating dark field microcopy setup, wherein the setup comprises a light source constructed to emit a beam of electromagnetic radiation at a specimen chamber, the chamber is constructed to hold the colloidal particles and to allow a portion of the beam to scatter from the particles, the scattered portion of the beam directed to a sensor, wherein the sensor is adapted to detect the electromagnetic radiation, the method comprising:
    a. preparing a plurality of samples with known particle sizes of known concentrations and;
    b. for each known particle size sample in the plurality:
       i. introducing the sample into the specimen chamber;
       ii. activating the light source;
       iii. measuring a scattered light intensity and a number of particles detected by the sensor;
    c. for each known particle size, determining calibrated investigated volume based on the known concentration, the measured scattering and the measured number of particles.

11. The method of claim 10, wherein the light source is altered to produce electromagnetic radiation at a plurality of wavelengths, the method further comprising;
    d. performing steps (a)-(c) for each wavelength in the plurality.

12. The method of claim 10, further comprising:
    d. introducing an unknown sample into the specimen chamber;
    e. activating the light source;
    f. for the plurality of particle sizes in the unknown sample:

i. measuring a number of particles detected by the sensor;
ii. calculating a particle size distribution based on the calibrated investigated volume and the measured number of particles from the unknown sample.

* * * * *